US010945596B2

(12) United States Patent
Marin et al.

(10) Patent No.: US 10,945,596 B2
(45) Date of Patent: Mar. 16, 2021

(54) METHOD FOR DETERMINING A DIOPTRIC PARAMETER OF AN OPHTHALMIC LENS TO BE PROVIDED TO A PERSON

(71) Applicant: ESSILOR INTERNATIONAL, Charenton-le-Pont (FR)

(72) Inventors: Gildas Marin, Charenton-le-Pont (FR); Jean-Luc Perrin, Charenton-le-Pont (FR); Martha Hernandez Castaneda, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 153 days.

(21) Appl. No.: 16/318,984

(22) PCT Filed: Jul. 18, 2017

(86) PCT No.: PCT/EP2017/068119
§ 371 (c)(1),
(2) Date: Jan. 18, 2019

(87) PCT Pub. No.: WO2018/015381
PCT Pub. Date: Jan. 25, 2018

(65) Prior Publication Data
US 2019/0261848 A1    Aug. 29, 2019

(30) Foreign Application Priority Data

Jul. 22, 2016    (EP) ..................................... 16305945

(51) Int. Cl.
*A61B 3/00*    (2006.01)
*A61B 3/14*    (2006.01)
(Continued)

(52) U.S. Cl.
CPC ............ *A61B 3/0025* (2013.01); *A61B 3/028* (2013.01); *A61B 3/032* (2013.01); *A61B 3/04* (2013.01)

(58) Field of Classification Search
CPC .. A61B 3/00; A61B 3/103; A61B 3/14; A61B 3/113; A61B 3/024; A61B 3/032;
(Continued)

(56) References Cited

U.S. PATENT DOCUMENTS

| 2002/0196412 A1* | 12/2002 | Abitbol | ................ G02C 7/028 351/246 |
| 2012/0229758 A1* | 9/2012 | Marin | ...................... G02C 7/02 351/159.52 |
| 2015/0342454 A1* | 12/2015 | Foster | .................... A61B 3/103 351/211 |

OTHER PUBLICATIONS

International Search Report and Written Opinion, dated Oct. 17, 2017, from corresponding PCT application No. PCT/EP2017/068119.

(Continued)

*Primary Examiner* — Dawayne Pinkney
(74) *Attorney, Agent, or Firm* — Nixon & Vanderhye (57) ABSTRACT

A method for determining a dioptric parameter includes: first, a test optical element having a dioptric function having a specific value of the dioptric parameter to be determined is provided and the person looks at a visual target using the test optical element; second, evaluation data and certitude data are collected, the evaluation data being indicative of the visual assessment expressed by the person looking at the visual target using the test optical element and certitude data being indicative of the degree of certainty of the person upon expressing the visual assessment. The first and second steps are repeated by varying the value of the dioptric parameter. For each value of the dioptric parameter tested a value a degree of certainty of the person is determined. The value of (Continued)

the dioptric parameter of the person is determined based on the values of degree of certainty of the person.

19 Claims, 2 Drawing Sheets

(51) Int. Cl.
*A61B 3/02* (2006.01)
*G02C 5/00* (2006.01)
*G02C 7/02* (2006.01)
*A61B 3/032* (2006.01)
*A61B 3/04* (2006.01)
*A61B 3/028* (2006.01)

(58) Field of Classification Search
CPC .. A61B 3/04; A61B 3/02; A61B 3/107; G02C 5/00; G02C 7/02; G02C 7/04
USPC ....... 351/246, 200, 205, 206, 209, 210, 222, 351/223, 227–230, 233, 239, 240, 243, 351/244, 247, 41, 159.01, 159.02
See application file for complete search history.

(56) References Cited

OTHER PUBLICATIONS

Diepes, Heinz: "Refraktionsbestimmung", Jan. 1, 2004 (Jan. 1, 2004), DOZ-Verlag Optische Fachveröffentlichungen GmbH, Heidelberg, pp. 238-252, XP002764592.

\* cited by examiner

METHOD FOR DETERMINING A DIOPTRIC PARAMETER OF AN OPHTHALMIC LENS TO BE PROVIDED TO A PERSON

FIELD OF THE INVENTION

The invention relates to a method for determining a dioptric parameter of a person, for example of an ophthalmic lens to be provided to a person and to a method for determining a dioptric sensitivity of a person corresponding to the sensitivity of the person to variation of a dioptric parameter of an ophthalmic lens to be provided to the person.

BACKGROUND OF THE INVENTION

Usually, a person wishing to have an optical equipment goes to see an eye care practitioner (ECP).

The determination of the wearer's prescription may require carrying out complex and time consuming measurements. Such measurements usually require complex and costing material and qualified personnel such as an eye care practitioner, to be carried out.

The classic measurements require great experience on the part of the eye care practitioner to be efficient and fast. Such measurements require that the eye care practitioner judges correctly the reactions of the person to evaluate the answers provided. Then, the results of the classic measurements are highly dependent on the eye care practitioner.

Existing adaptive psychophysical procedures, for example the staircases, constant stimuli, Psi algorithm procedures are powerful tools for determining a perceptual threshold such as sharpness or contrast and could be good alternatives to estimate the prescription of a person quickly and in an accurate manner. However, such methods are either too long or unsuitable when the person is uncertain and gives random or wrong answers, for being used by an eye care practitioner to measuring the prescription of a person. Such methods are even more long and not adapted when it is needed to perform a highly accurate dioptric parameter determination, for instance when it is needed to perform a measurement with a power step lower than 0.25D.

Therefore, there is a need for a method that would allow measuring more efficiently at least part of the prescription of a person.

One object of the present invention is to provide such method.

SUMMARY OF THE INVENTION

To this end, the invention proposes a method for determining a dioptric parameter of a person, for example of an ophthalmic lens to be provided to a person, the method comprising:
- a set-up step, during which a test optical element having a dioptric function having a specific value of the dioptric parameter to be determined is provided to the person and the person is required to look at a visual target using the test optical element,
- a data collecting step, during which evaluation data and certitude data are collected, the evaluation data being indicative of the visual assessment expressed by the person looking at the visual target using the test optical element and certitude data being indicative of the degree of certainty of the person upon expressing the visual assessment, wherein the set-up and data collecting steps are repeated by varying the value of the dioptric parameter of the test optical element, and the method further comprises:
- a global analyzing step, during which for each value of the dioptric parameter tested during the set-up and data collecting step a value a degree of certainty of the person is determined and the value of the dioptric parameter of the person is determined based on the values of degree of certainty of the person.

Advantageously, the method of the invention allows improving the measurements of the dioptric parameters of a person by making such measurements more precise, faster and more robust.

Making the measurements faster allows reducing the fatigue and the stress of the person, which could alter the measurements.

Furthermore, the method of the invention may provide an indication of the dioptric sensitivity of a person corresponding to the sensitivity of the person to variation of a dioptric parameter of an ophthalmic lens to be provided to the person and may provide a good acceptation at new dioptric parameter.

According to further embodiments which can be considered alone or in combination:
- during the global analyzing step a range of certainty is determined, the range of certainty corresponding to a range of values of the dioptric parameter for which the degree of certainty of the person is within a predetermined range of values, for example 50%; and/or
- the global analyzing step further comprises determining a first and a second dioptric parameter values corresponding to the lower limit and the upper limit of the range of certainty and where the value of the dioptric parameter of the person is determined from the first and a second dioptric parameter values; and/or
- the value of the dioptric parameter is determined from a representative curve of said degrees of certainty based on the tested value of the dioptric parameter and a predefined value of degree of certainty; and/or
- the global analyzing step further comprises determining an interpolation of the representative curve of said degrees of certainty and wherein the value of the dioptric parameter of the person is determined from said interpolation; and/or
- the global analyzing step further comprises fitting a parametric function to the representative curve of said degrees of certainty and wherein the value of the dioptric parameter of the person is determined from the parameters of said fit parametric function; and/or
- the set-up and collecting steps are repeated at least until obtaining at least three different values of degree of certainty of the person and/or the set-up and collecting steps have been repeated a number of time equal to a predetermined value; and/or
- the visual assessment expressed by the person corresponds to an indication of a preferred visual state among two visual states; and/or
- the method further comprises an intermediate analyzing step that is repeated with the set-up and data collecting steps, during the intermediate analyzing step at least the evaluation data is analyzed to determine a value of the dioptric parameter of the test optical element to be provided to the person during the next set-up step; and/or
- during the intermediate analyzing step the value of the dioptric parameter of the test optical element to be provided to the person during the next set-up step is further determined by analyzing the certitude data; and/or during the intermediate analyzing step an intermediate value of the degree of certainty for the corresponding tested value of the dioptric parameter is determined based on all the previous certitude data collected for said tested value of the dioptric parameter; and/or during the intermediate analyzing step an intermediate range of certainty is determined, the intermediate range of certainty corresponding to a range of values of the dioptric parameter for which the intermediate degree of certainty of the person is within a predetermined range of values; and/or the value of the dioptric parameter of the test optical element to be provided to the person during the next set-up step is further based on the intermediate value of the degree of certainty and/or the intermediate range of certainty; and/or the set-up and collecting steps are repeated at least until the difference between two consecutive intermediate ranges of certainty is smaller or equal to a predetermined value, for example 0.05 D; and/or the set-up and collecting steps are repeated at least until the difference between two consecutive values of the dioptric parameter of the test optical element is smaller or equal to a predetermined value, for example 0.05 D; and/or the set-up and collecting steps are repeated at least until the number of time the direction of variation of the value of the dioptric parameter between two subsequent set-up step has reached a predetermined number, for example 2, 4 or 6; and/or the certitude data are expressed on a scale of at least two levels; and/or the certitude data are a subjective degree of certainty and/or an objective degree of certainty; and/or the dioptric parameter corresponds to the spherical and/or cylinder power and/or axis and/or prism and/or addition and/or a range of certainty associate with one of the spherical and/or cylinder power and/or axis and/or prism and/or addition; and/or the certitude data are based on a model for estimating the level of certainty from the acoustic parameters of a voice expression of the person; and/or the certitude data are based on a measurement of the time the person takes to express the visual assessment: and/or the person expresses the visual assessment by exerting pressure on a pressure sensor and wherein the certitude data is based on a measure of the intensity of pressure on said pressure sensor by the person; and/or during the set-up step the visual target is presented only once to the person.

during the set-up step the visual target is presented at least twice to the person; and/or for each value of the dioptric parameter a value of degree of certainty of the person is determined as the average value of the certainty data collected for such value of the dioptric parameter.

The invention also relates to a method for determining a dioptric sensitivity of a person corresponding to the sensitivity of the person to variation of a dioptric parameter of an ophthalmic lens to be provided to the person, the method comprising:

a set-up step, during which a test optical element having a dioptric function having a specific value of the dioptric parameter to be determined is provided to the person and the person is required to look at a visual target using the test optical element, a data collecting step, during which evaluation data and certitude data are collected, the evaluation data being indicative of the visual assessment expressed by the person looking at the visual target using the test optical element and certitude data being indicative of the degree of certainty of the person upon expressing the visual assessment, wherein the set-up and data collecting steps are repeated by varying the value of the dioptric parameter of the test optical element, and the method further comprises:

a global analyzing step, during which for each value of the dioptric parameter tested during the set-up and data collecting step a value a degree of certainty of the person is determined and the value of the dioptric sensitivity of the person is determined based on a range of certainty corresponding to a range of values of the dioptric parameter for which the degree of certainty of the person is within a predetermined range of values.

The invention further relates to a computer program product comprising one or more stored sequences of instructions that are accessible to a processor and which, when executed by the processor, causes the processor to carry out at least the steps of the method according to the invention.

The invention also relates to a computer-readable storage medium having a program recorded thereon; where the program makes the computer execute at least the data collecting step and the global analyzing steps of the method of the invention.

The program recorded on computer-readable storage medium of the invention may make the computer further execute the intermediate analyzing step.

The invention further relates to a device comprising a processor adapted to store one or more sequence of instructions and to carry out at least steps of the method according to the invention.

BRIEF DESCRIPTION OF THE DRAWINGS

Embodiments of the invention will now be described, by way of example only, and with reference to the following drawings in which.

DETAILED DESCRIPTION OF PREFERRED EMBODIMENTS

The method of the invention is for determining a dioptric parameter of a person, for example of an ophthalmic lens to be provided to a person.

The dioptric parameter may correspond to the spherical and/or cylinder power and/or axis and/or prism and/or addition of the ophthalmic device, for example ophthalmic lenses, to be provided to the person.

The method of the invention may also allow determining a range of certainty or sensitivity, associated with one of the spherical and/or cylinder power and/or axis and/or prism and/or addition of the ophthalmic device, for example ophthalmic lenses, to be provided to the person.

Figure 1:
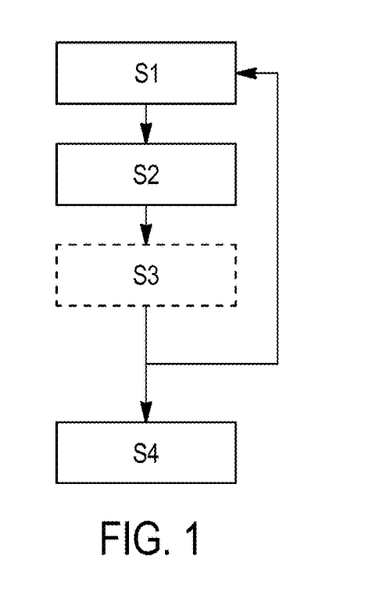
FIG. 1 is a flow chart representing according to the invention.

As illustrated on FIG. 1, the method of the invention comprises at least:
- a set-up step S1,
- a data collecting step S2, and
- a global analyzing step S4.

During the set-up step S1 a test optical element having a dioptric function having a specific value of the dioptric parameter to be determined is provided to the person. The person is then asked to look at a visual target using the test optical element.

The person may conduct this test monocularly or binocularly.

A binocular test may be preferred as it would reduce errors due to accommodation, and so increase accuracy. In this case, the dioptric parameter is determined for a single eye, but the visual target is seen binocularly, and it is preferred to start with the non dominant eye.

During the set-up step S1 known refractive measurements may be carried out. For example, a Jackson Cross Cylinder protocol or a Duochrome test may be implemented during the set-up test.

For example, the test optical element may be an ophthalmic lens having a specific sphere and the visual target may be a trichromic image, such as black letters or characters on a red/green background. The person is asked to look at the visual target using the ophthalmic lens.

According to an embodiment of the invention, during the set-up step the visual target is presented only once to the person.

Alternatively, during the set-up step the visual target is presented at least twice to the person.

During the data collecting step S2 evaluation data and certitude data are collected.

The evaluation data are indicative of the visual assessment expressed by the person looking at the visual target using the test optical element.

For example, the visual assessment expressed by the person corresponds to an indication of a preferred visual state among two visual states presented at the person.

The person may be required to compare the visual state of looking at a visual target using the test optical element provided during the set-up step with a reference visual state. The reference visual state may correspond to looking directly at the visual target without any test optical element.

The person may be looking at two visual targets at the same time and the visual assessment expressed by the person may correspond to one of the visual targets.

For example, if the user is to look at a red target comprising red characters on a black background and a green target comprising the same character in green on a black background, the visual assessment may consist in an indication of one of the targets.

The certitude data are indicative of the degree of certainty of the person upon expressing the visual assessment.

For example, the person when expressing the visual assessment may provide an answer corresponding to the fact that the person does not know, for example the person does not make a difference between two visual states or visual targets.

According to an embodiment of the invention, the certitude data are expressed on a scale of at least two levels.

The certitude data may have a binary value corresponding to the fact that the person is certain of the stated visual assessment or that the person cannot make a visual assessment.

The certitude data may further be expressed on a scale comprising a greater number of levels from "absolutely certain" to "totally uncertain". For example, the certitude data may be expressed on a scale from 0 to 100. The number of levels of the certitude scale is advantageously smaller than or equal to 5 so as limit the number of choice of the person and to avoid to confuse the person with a too great number of choice.

The certitude data may correspond to a subjective level of certainty. In other words, the certitude data may correspond to a level of certainty directly expressed by the person. For example, the person upon expressing the visual assessment, further expresses a level of certainty associated with the visual assessment.

According to an embodiment of the invention the certitude data may correspond to an objective degree of certainty. The objective level of certainty may be obtained, for example measured or determined, from the way the person expresses the visual assessment.

For example, the certitude data may be based on a model for estimating the level of certainty from the acoustic parameters of a voice expression of the person. In other words, by analyzing (spectral or intensity) the voice of the person upon expressing the visual assessment it is possible to determine the level of certainty of the person.

The certitude data may be determined by measuring of the time duration the person takes to express the visual assessment after the visual stimulus is provided to him/her. Typically, the longer it takes the person to provide a visual assessment the lower the certainty level may be and the shorter it takes the person to provide a visual assessment the higher the certainty level may be.

According to an embodiment of the invention, the person expresses the visual assessment by exerting pressure on a pressure sensor. The certitude data may be based on a measure of the intensity of pressure exerted by the person on said pressure sensor.

As illustrated on FIG. 1, the set-up and data collecting steps are repeated by varying the value of the dioptric parameter of the test optical element.

The set-up and data collecting steps may be repeated a number of time equal to a predetermined value. For example, the method of the invention may be implemented with a predetermined number of measurements, for example between 4 and 10 measurements.

The number of times the set-up and data collecting steps are repeated may be determined based on further data determined either during the global analyzing step or during an intermediate analyzing step. Examples of such embodiments are details further in the description.

During the global analyzing step S4 a degree of certainty of the person is determined for each value of the dioptric parameter tested during the set-up and data collecting step a value. The values of degree of certainty of the person are processed to determine the value of the dioptric parameter of the person, for example the dioptric parameter of the ophthalmic lens to be provided to the person.

The value of the degree of certainty of the person for a given value of tested dioptric parameter may correspond to the average value of the certainty data collected for said tested dioptric parameter. For example, when repeating the set-up and data collecting steps different values of the tested dioptric parameter are tested a plurality of times and for each test a certainty data is collected. The degree of certainty may be determined based on a combination of such collected data.

For example, for each value of the dioptric parameter a value of degree of certainty of the person is determined as the average value of the certainty data collected for such value of the dioptric parameter.

The data collected during the data collecting step may further be analyzed to determine a range of certainty. The range of certainty corresponds to a range of values of the dioptric parameter for which the degree of certainty of the person is within a predetermined range of values, for example 50%. Typically, the range of certainty corresponds to a range of values of the dioptric parameter for which the person does not assess a visual change.

A range of certainty may be used to determine the value of the dioptric parameter of the ophthalmic lens to be provided to the person.

For example, during the global analyzing step a first and a second dioptric parameter values corresponding to the lower limit and the upper limit of the range of certainty are determined. The value of the dioptric parameter of the ophthalmic lens to be provided to the person is determined from the first and a second dioptric parameter values, for example, said value of the dioptric parameter is determined based on the average value of the first and second dioptric parameter values.

The value of the dioptric parameter of the ophthalmic lens to be provided to the person may further be determined based on a representative curve of the degrees of certainty according to the tested values of the dioptric parameter and a predefined value of degree of certainty.

The representative curve of the degrees of certainty may be interpolated so as to determine the value of the dioptric parameter of the ophthalmic lens to be provided to the person.

The global analyzing step may further comprise fitting a parametric function to the representative curve of said degrees of certainty. The value of the dioptric parameter of the person may then be determined from the parameters of said fit parametric function.

The set-up and data collecting steps may be repeated at least until obtaining at least three different values of degrees of certainty of the person.

As illustrated on FIG. 1, the method of the invention may further comprise the intermediate analyzing step S3 that is repeated with the set-up and data collecting steps.

During the intermediate analyzing step S3 at least the evaluation data is analyzed to determine a value of the dioptric parameter of the test optical element to be provided to the person during the next set-up step.

For example, with the duochrome test (described later in this document), if the person's answers change from preferring the red visual target to the green visual target, the direction of variation of the value of the sphere between two set-up steps may be reversed.

According to an embodiment of the invention, the set-up and collecting steps are repeated at least until the difference between two consecutive values of the dioptric parameter is smaller or equal to a predetermined value, for example 0.0625 D.

In the sense of the invention "two consecutive values of the dioptric parameter" is to be understood as the values of the dioptric parameter of the test optical element in two consecutive set-up steps of the method of the invention.

According to a further embodiment of the invention, the set-up and collecting steps are repeated at least until the number of time the direction of variation of the value of the dioptric parameter between two subsequent set-up steps has reached a predetermined number, for example 2, 4 or 6.

To increase the efficiency of the method of the invention during the intermediate analyzing step the value of the dioptric parameter of the test optical element to be provided to the person during the next set-up step is further determined by analyzing the certitude data.

For example, with the duochrome test, if two consecutive person's answers change from preferring the red visual target to the green visual target, but the last answer indicating a preference for the green target is associated with a certitude data that indicates that the person is not sure of it assessment, the direction of variation of the value of the sphere between two set-up step may be maintained although the visual assessment of the person has changed.

An intermediate value of the degree of certainty for the corresponding tested value of the dioptric parameter may be determined during the intermediate analyzing step. The intermediate value of degree of certainty may be based on all the previous certitude data collected for said tested value of the dioptric parameter. As for the degree of certainty the intermediate value of the degree of certainty may be determined as the average value of the certitude data.

Furthermore, an intermediate range of certainty is determined, the intermediate range of certainty corresponding to a range of values of the dioptric parameter for which the intermediate degree of certainty of the person is within a predetermined range of values.

The value of the dioptric parameter of the test optical element to be provided to the person during the next set-up step may further be based on the intermediate value of the degree of certainty and/or the intermediate range of certainty.

For example, the set-up and collecting steps are repeated at least until the difference between two consecutive intermediate ranges of certainty is smaller or equal to a predetermined value, for example 0.0625 D.

In the sense of the invention "two consecutive intermediate ranges of certainty" is to be understood as the intermediate ranges of certainty determined in two consecutive intermediate analyzing step S3.

Figure 2:
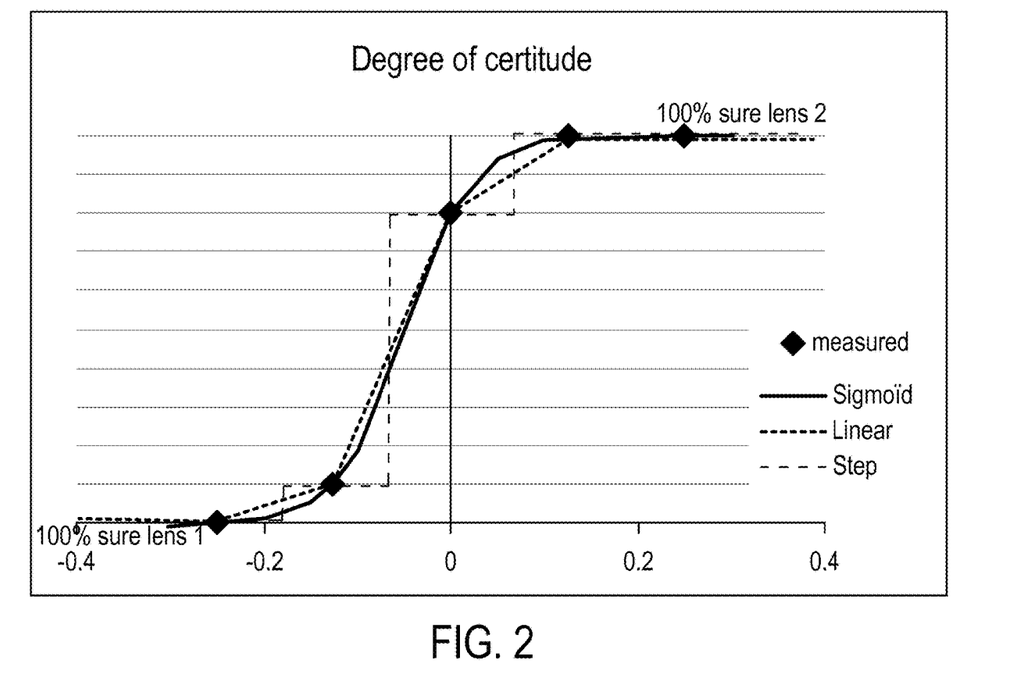
FIG. 2 is a graphic representation of a certitude curve according to the invention.

FIG. 2 illustrates an example of determination of the value of the dioptric parameter of the test optical element to be provided to the person during the next set-up step.

A solution according to an embodiment of the invention is to estimate at each reversal of the value of the tested dioptric parameter the position and the size of the intermediate range of certainty of the person, i.e. the high level and low level position or, in other words, the high and low limits of the "don't know" answers.

The gap between the values of the dioptric parameter of the test optical element in two consecutive set-up steps may be adapted to the size of the intermediate range of certainty of the person: typically, the gap is adjusted to the half of the estimated size of the intermediate range of certainty of the person or eventually equal to the size multiplied or divided by an adaptive ratio for a faster or a better estimation.

To estimate the position and size of the intermediate range of certainty of the person, at each reversal of the value of the tested dioptric parameter, the probability of answers may be determined for each possible value as follows:

for each tested value, count +1 for answer 1 (lens 1 or Red . . . ), −1 for answer 2 (lens 2 or green . . . ) and 0 for "don't know".

then, answers between tested values may be interpolated using step, linear, sigmoid, polynomial or any other kind of function.

For example, using a step interpolation, count +1 for all values above high reversals-step/2 and −1 below low reversals+step/2. Then, interpolate the answer for all values between −step/2 and +step/2 of each tested value.

Probabilities of answers for each value may then be the number of count divided by the maximum count per value. This gives a number between −100% and +100%.

The intermediate range of certainty may be defined by a high level and a low level that are the 2 bounds for which intermediate degree of certainty is at −50% and +50%. The range of certainty or the sensitivity of the person may be defined to be the half of the intermediate range of certainty. The final value is the center of the intermediate range of certainty of 0%.

A reversal is a point of comparison where the direction of variation of the tested dioptric parameter deducted from the person answer is changing (reversed) from increase to decrease or the contrary.

After each reversal, the intermediate degree of certainty may be re-evaluated on the full range of variation of the tested dioptric parameter. A new estimation of the sensitivity of the person and the best parameter value can be found. With this procedure, all the answers expressed by the person contribute to the final value and best parameters estimation.

After the first estimation of the range of certainty, a reversal inside the range of certainty may be cancelled to remove random answer effect and make sure all the real range of certainty is evaluated.

A trial is the elementary process where the person evaluates if the current value is acceptable or not usually done by one comparison from which we deduct the correct direction of variation to improve the acceptability.

The gap is the change applied to the value of the tested dioptric parameter between 2 consecutive set-up steps. After each reversal, the gap is adapted by a coefficient (step_ratio) from the sensitivity of the person, a minimum and a maximum variation and a minimum value allowed.

For example, for the Jackson Cross Cylinder, preference for lens 1 or lens 2, or for the Duochrome test, preference for red or green, may give the direction of variation to apply.

Answers of the person may be typically of 3 types: lens1 (or position1/red/right/top . . . ), lens2 (or position2/green/left/bottom . . . ), "I don't know"/"no differences" and can be recovered with a 3 touch pad or a wheel pad with a click (left/right+don't know by clicking) or a microphone that records oral answers or any other interface. Alternatively, answers may be recorded by the ECP.

The answers requested may be more complete including a certainty level in a given range [−n;n].

For example, [−2; −1; 0; +1; +2]: −2: lens1 choice for sure; −1: lens 1 choice, not sure; 0: don't know; +1: lens2 choice, not sure; +2: lens2 choice for sure.

Typically, the number of answers may include, but is not limited to, 5 levels of certainty: sure; almost sure; not sure; maybe; don't know combined with 2 choices (lens1/lens2, position 1/position2, red/green, left/right . . . ).

The person has only 2 possible answers: lens1(+1) or lens2 (−1). In case no other certainty data are collected, it is proposed to make this test at least twice for the same parameter value, and to determine the certainty data from the discrepancy between answer given for the same dioptric parameter value.

For example, if each parameter is tested 3 times, if all answers are lens1, uncertainty is +1 (⅓+⅓+⅓), if 2 answers are lens1 and one answer is lens2, uncertainty is ⅓ (⅓+⅓−⅓). Such example of embodiment is illustrated on FIG. 3.

Figure 3:
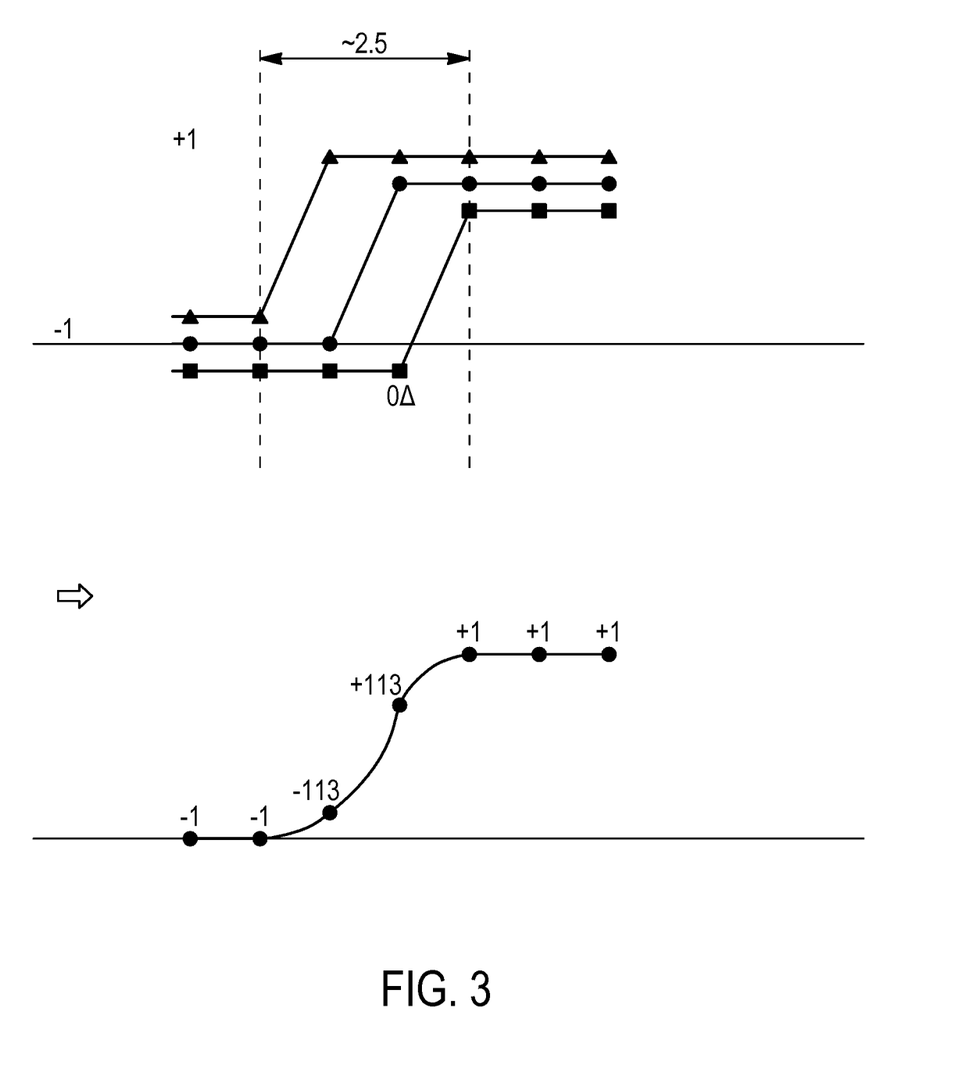
FIG. 3 illustrates a determination of the degree of certitude according to an embodiment of the invention.

It is also possible to determine degree of certainty from the range of values of the dioptric parameter for which for each 3 tests, the answer is the same, such range is dot lines in FIG. 3.

EXAMPLES

Starting Values

Typically, the starting values for the dioptric parameters are derived from an objective measurement, made with an autorefractometer (ex: AKR/ARK systems from Nidek or KR/RM systems from Topcon) or a retinoscopy or from habitual correction measured from the current equipment with a focimeter.

The preferred starting value is from an autorefractometer for the cylinder and axis and from a fog/defog procedure conducted by an optometrist or ECP for sphere.

The starting value for the gap between two tested values is usually 0.25D but may be derived from a preliminary measure of person sensitivity such as High Order Aberration (HOA), RMS level from an aberrometer, Blur detection threshold or a dioptric sensitivity measured with a Duochrome test or with displayed letters.

Example for Determining the Person Sensitivity to Blur

The person sits 6 meters from a screen in a room lit normally.

The person uses its usual ophthalmic correction, for example its usual ophthalmic lenses.

The person's understanding of the following instruction is confirmed: "Letters will be presented to you. They are clear and become increasingly blurred. We will ask you to provide us, for example with the keyboard when the blur becomes unacceptable for you. This is the amount of blur that you refuse to tolerate if you suffer it permanently. We ask you to indicate the first unacceptable blur value. Then, the letters will be presented blur, they will become increasingly clear. We will ask you to provide us, for example with the keyboard, when the letters are clear".

A random time is chosen to display images, permitting variation of 1D between 20 to 40 s.

An image display blurs in an increasingly manner but with an undetectable gap for example <0.05D.

The person reports that it has detected blur.

A second measurement is made by reducing the blur, the person should report when it no longer sees the blur.

These steps may be repeated 3 times.

Example of the Duochrome Test

The person sits at 6 meters of a screen.

The person uses its usual ophthalmic correction, for example its usual ophthalmic lenses.

A set of duochrome targets is provided.

The left eye of the person is hidden.

0.12D correction sphere value is added on the right eye of the person.

The person is asked "if he/she sees a difference between the red and green visual targets"

The person's answer is collected.

−0.12D correction sphere value is added to the right eye of the person.

The person is asked "if he/she sees differences between the red and green visual targets"

The person's answer is collected.

If no difference is detected by the person, the steps are repeated with ±0.25D.

The steps are repeated with the left eye of the person.

Example of the Jackson Cross Cylinder Protocol

For evaluating a cylinder correction, it is recommended to use a Jackson Cross Cylinder (JCC) protocol where cylinder power and axis are tested sequentially in a vectorial manner. Thus, the axis is converted in terms of vectorial components having the same dimension as the cylinder power (see vectorial representation in J0-J45). In this representation, the cylinder corresponds to a vector which module equals the cylinder power and which orientation corresponds to twice the cylinder angle. Each component is tested separately.

The direction is deducted from the person answers as follows:

If lens 1 is preferred, the tested component is increased;
If lens 2 is preferred, the tested component is decrease.

The CC value (val_CC) corresponds to the cylinder used for the JCC procedure:

Nul spherical equivalent
Power of +/−val_CC (ie cylinder of 2×CC_value)

Val_CC=0.33D is recommended but modifying this parameter from 0.12 to 1D should be allowed.

During all the process, the spherical equivalent is maintained constant.

If possible the answer of the person should be registered directly with a keypad or other allowing 3 types of answer: lens 1 (or left), lens 2 (or right), "don't know or same" (middle or both right and left)

An additive process is needed to allow going from lens 1 to lens 2. Any of the previous key or combination may be used An alternative could be: the person goes from lens 1 to lens 2 alternatively and stops on the preferred lens (one answer) or chose "don't know".

The "don't know" answer is translated as "same answer as last answer" before any processing regarding to inversion in the answers.

If first answer is "don't know", a modification of the initial value is requested, for example, ask the optometrist to adjust the initial value or try alternatively one direction and the other.

A sound may be played as feedback for the person the answer has been taken into account. The display or a sound feedback indicates to the person whether currently lens 1 or lens 2 is shown, for example display a sign/bar on left or right corresponding to the side to answer if chosen.

The displayed stimulus may be the Maltese points typically used for a JCC procedure.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for determining a dioptric parameter of a person, the method comprising:
a set-up step, during which a test optical element is provided to the person and the person is required to look at a visual target using the test optical element, the test optical element having a dioptric function configured in accordance with a dioptric parameter to be tested; and
a data collecting step, during which evaluation data and certitude data are collected by a computer device equipped with a processor that operates in accordance with instructions stored on a non-transitory storage medium in communication with said processor, the evaluation data being indicative of a visual assessment expressed by the person looking at the visual target using the test optical element, and the certitude data being indicative of a degree of certainty for the visual assessment as expressed by the person,
wherein the set-up and data collecting steps are repeated with a plurality of values for the dioptric parameter of the test optical element, and
wherein the method further comprises, after the repeated set-up and data collecting steps:
a global analyzing step executed by the computer device, during which values of the degree of certainty of the person are respectively determined by the computer device for each one of the plurality of values of the dioptric parameter tested and collected by the computer device during the repeated set-up and data collecting steps, and a value of the dioptric parameter of the person is determined by the computer device based on the values of the degree of certainty of the person determined by the computer device.

2. The method according to claim 1, wherein during the global analyzing step a range of certainty is determined, the range of certainty corresponding to a range of values of the dioptric parameter for which the degree of certainty of the person is within a predetermined range of values.

3. The method according to claim 2, wherein the global analyzing step further comprises determining first and second dioptric parameter values corresponding to a lower limit and an upper limit of the range of certainty, and where the value of the dioptric parameter of the person is determined from the first and second dioptric parameter values.

4. The method according to claim 1, wherein the set-up and collecting steps are repeated at least until at least three different values of degree of certainty of the person are obtained and/or the set-up and collecting steps have been repeated a number of time equal to a predetermined value.

5. The method according to claim 1, further comprising:
an intermediate analyzing step, executed by the computer device, and repeated with the set-up and data collecting steps,
wherein during the intermediate analyzing step, at least the evaluation data collected by the computer device is analyzed by the computer device to determine a next value of the dioptric parameter to be tested during a next set-up step.

6. The method according to claim 5, wherein during the intermediate analyzing step, the next value of the dioptric parameter to be tested during the next set-up step is further determined by analyzing the collected certitude data.

7. The method according to claim 5, wherein during the intermediate analyzing step, an intermediate value of the degree of certainty for the corresponding tested value of the dioptric parameter is determined based on all previous certitude data collected for said tested value of the dioptric parameter.

8. The method according to claim 7, wherein during the intermediate analyzing step, an intermediate range of certainty is determined, the intermediate range of certainty corresponding to a range of values of the dioptric parameter for which the intermediate degree of certainty of the person is within a predetermined range of values.

9. The method according to claim 7, wherein the next value of the dioptric parameter to be tested during the next set-up step is further based on the intermediate value of the degree of certainty and/or the intermediate range of certainty.

10. The method according to claim 1, wherein the dioptric parameter corresponds to the spherical and/or cylinder power and/or axis and/or prism and/or addition and/or a range of certainty associated with one of the spherical and/or cylinder power and/or axis and/or prism and/or addition.

11. The method according to claim 1, wherein the certitude data are based on a model for estimating a level of certainty from acoustic parameters of a voice expression of the person.

12. The method according to claim 1, wherein the certitude data are based on a measurement of a time duration taken by the person to express the visual assessment after the visual target is presented to the person.

13. The method according to claim 1,
wherein the person expresses the visual assessment by exerting pressure on a pressure sensor, and
wherein the certitude data is based on a measure of an intensity of pressure exerted by the person on said pressure sensor.

14. The method according to claim 1, wherein during the set-up step, the visual target is presented at least twice to the person.

15. The method according to claim 1, wherein the value of the dioptric parameter is determined from a representative curve of said degrees of certainty based on the tested value of the dioptric parameter and a predefined value of degree of certainty.

16. The method according to claim 15, wherein the global analyzing step further comprises determining an interpolation of the representative curve of said degrees of certainty and wherein the value of the dioptric parameter of the person is determined from said interpolation.

17. The method according to claim 15, wherein the global analyzing step further comprises fitting a parametric function to the representative curve of said degrees of certainty and wherein the value of the dioptric parameter of the person is determined from the parameters of said fit parametric function.

18. The method according to claim 1, wherein for each one of the plurality of values of the dioptric parameter tested, a value of the degree of certainty of the person is determined as an average value of the certainty data collected for such value of the dioptric parameter.

19. A method for determining a dioptric sensitivity of a person corresponding to the sensitivity of the person to variation of a dioptric parameter of an ophthalmic lens to be provided to the person, the method comprising:
a set-up step, during which a test optical element is provided to the person and the person is required to look at a visual target using the test optical element, the test optical element having a dioptric function configured in accordance with a dioptric parameter to be tested; and
a data collecting step, during which evaluation data and certitude data are collected by a computer device equipped with a processor that operates in accordance with instructions stored on a non-transitory storage medium in communication with said processor, the evaluation data being indicative of a visual assessment expressed by the person looking at the visual target using the test optical element, and the certitude data being indicative of the degree of certainty for the visual assessment as expressed by the person,
wherein the set-up and data collecting steps are repeated with a plurality of values for the dioptric parameter of the test optical element, and
wherein the method further comprises:
a global analyzing step executed by the computer device, during which values of the degree of certainty of the person are respectively determined by the computer device for each one of the plurality of values of the dioptric parameter tested and collected by the computer device during the repeated set-up and data collecting steps, and a value of the dioptric sensitivity of the person is determined by the computer device based on a range of certainty corresponding to a range of values of the dioptric parameter for which the degree of certainty of the person determined by the computer device is within a predetermined range of values.

* * * * *